(12) United States Patent
Palhan et al.

(10) Patent No.: US 10,253,356 B2
(45) Date of Patent: Apr. 9, 2019

(54) VISUALIZING MODIFIED NUCLEOTIDES AND NUCLEIC ACID INTERACTIONS IN SINGLE CELLS

(71) Applicant: SIGMA-ALDRICH CO. LLC, St. Louis, MO (US)

(72) Inventors: Vikas Palhan, Ballwin, MO (US); Carol Kreader, Kirkwood, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 43 days.

(21) Appl. No.: 15/534,334

(22) PCT Filed: Dec. 22, 2015

(86) PCT No.: PCT/US2015/067316
§ 371 (c)(1),
(2) Date: Jun. 8, 2017

(87) PCT Pub. No.: WO2016/106298
PCT Pub. Date: Jun. 30, 2016

(65) Prior Publication Data
US 2017/0362647 A1    Dec. 21, 2017

Related U.S. Application Data

(60) Provisional application No. 62/095,660, filed on Dec. 22, 2014, provisional application No. 62/109,979, filed on Jan. 30, 2015.

(51) Int. Cl.
| | | |
|---|---|---|
| *C12Q 1/68* | (2018.01) | |
| *C12Q 1/6841* | (2018.01) | |
| *C12N 15/09* | (2006.01) | |
| *G01N 33/50* | (2006.01) | |

(52) U.S. Cl.
CPC ........... *C12Q 1/6841* (2013.01); *C12N 15/09* (2013.01); *G01N 33/50* (2013.01); *C12Q 2525/117* (2013.01); *C12Q 2533/107* (2013.01); *C12Q 2565/601* (2013.01)

(58) Field of Classification Search
None
See application file for complete search history.

(56) References Cited

U.S. PATENT DOCUMENTS

2007/0178476 A1    8/2007    Shima et al.

OTHER PUBLICATIONS

Gomez et al., "Detection of histone modifications at specific gene loci in single cells in histological sections", Nature Methods, 10 (2) 171-177 (2013).
Nasserkort et al., "Aberrant septin 9 DNA methylation in colorectal cancer is restricted to a single CpG island", BMC Cancer 2013, 13:398.
Weibrecht et al., "In situ detection of individual mRNA molecules and protein complexes or post-translational modifications using padlock probes combined with the in situ proximity ligation assay", Nature Protocols 8.2 (2013): 355-372.
International Search Report for PCT/US2015/67316 dated May 6, 2016 (5 pages).

*Primary Examiner* — James Martinell
(74) *Attorney, Agent, or Firm* — Benjamin J. Sodey

(57) ABSTRACT

Methods for visualizing modified nucleotides in a specific nucleic acid sequence or specific nucleic acid sequence interactions in single cells, wherein the methods comprise coupling an in situ hybridization (ISH) reaction with a proximity ligation assay (PLA) reaction.

14 Claims, 5 Drawing Sheets
(3 of 5 Drawing Sheet(s) Filed in Color)
Specification includes a Sequence Listing.

GCGTCGCCCGTCCCTGGCTTCTCTGACAGCCGTGTTCCATCCCCGCCCTGTGCCCCTTCTCCCG
GACAGTGCCTTCTCCAGGGCTCACCCAGGAGGGTGCAGCGGTGGCCCCGGGGCGGTGGTCGTG
GTGGGGTGTTAGCTGCAGGGGTGCCCTCGGTGGGTGGGAGTTGGTGGCCTCTCGCTGGTGCCA
TGGGACTCGCATGTTCGCCCTGCGCCCTCGGCTCTTGAGCCCACAGGCCGGGATCCTGCCTGC
CAGCCGCGTGCGCTGCCGTTTAACCCTTGCAGGCGCAGAGCGCGCGGCGGCGGTGACAGAGAAC
TTTGTTTGGCTGCCCAAATACAGCCTCCTGCAGAAGGACCCTGCGCCCGGGAAGGGGAGGAAT
CTCTTCCCCTCTGGGCGCCCGCCCTCCTCGCCATGGCCCGGCCTCCACATCCGCCCACATCT*GG*
*CCGCAGCGGGCGCCCGGGGGAGGGGCTGAGGCCGCGTCTCTCGCCGTCCCCTGGGCGCGGGC*
*CAGGCGGGGAGGAGGGGGCGCTCCGGTCGTGTGCCCAGGACTGTCCCCAGCGGCCACTCGGG*
*CCCCAGCCCCCAGGCCTGGCCTTGACAGGCGGGCGGAGCAGCCAGTGCGAGACAGGGAGGCCG*
*GTGCGGGTGCGGGAACCTGATCCGCCCGGGAGGCGGGGCGGGGCGGGGCGCAGCGCGCGGGG*
*AGGGGCCGGCGCCCGCCTTCC*TCCCCCATTCATTCAGCTGAGCCAGGGGGCCTAGGGGCTCCTC
CGGCGGCTAGCTCTGCACTGCAGGAGCGCGGGCGCGGCGCCCCAGCCAGCGCGCAGGGCCCGGG
CCCCGCCGGGGCGCTTCCTCGCCGCTGCCCTCCGCGCGACCCGCTGCCCACCAGCCATCATGT
CGGACCCCGCGGTCAACGCGCAGCTGGATGGGATCATTTCGGACTTCGAAGGTGGGTGCTGGGC
TGGCTGCTGCGGCCGCGGACGTGCTGGAGAGGACCCTGCGGGTGGGCCTGGCGCGGGACGGGGG
TGCGCTGAGGGGAGACGGGAGTGCGCTGAGGGGAGACGGGACCCCTAATCCAGGCGCCCTCCCG
CTGAGAGCGCCGCGCGCCCCGGCCCCGTGCCCGCGCCGCCTACGTGGGGGACCCTGTTAGGGG
CACCCGCGTAGACCCTGCGCGCCCTCACAGGACCCTGTGCTCGTTCTGCGCACTGCCGCCTGGG
TTTCCTTCCTTTTATTGTTGTTTGTGTTTGCCAAGCGACAGCGACCTCCTCGAGGGCTCGCGAG
GCTGCCTCGGAACTCTCCAGGACGCACAGTTTCACTCTGGGAAATCCATCGGTCCCCTCCCTTT
GGCTCTCCCCGGCGGCTCTCGGGCCCCGCTTGGACCCGGCAACGGGATAGGGAGGTCGTTCCTC
ACCTCCGACTGAGTGGACAGCCGCGTCCTGCTCGGGTGGACAGCCCTCCCCTCCCCCACGCCAG
TTTCGGGGCCGCCAAGTTGTGCAGCCCGTGGGCCGGGAGCACCGAACGGACACAGCCCAGGTCG
TGGCAGGGTCTAGAGTGGGATGTCCCATGGCCCCATCCAGGCCTGGGGATATCCTCATCCGCC
TCCCAGAATCGGGCCGTGGGGACAGAAGGGCCTGCGTGCGGGCAGGGAGAGTATTTTGGCTC
TCTCCTGTCTTCGGGGTTTACAAAGTGTGTTGGGACTTGCGGGGCTGCTCTGTCCAAGCCTGGG
TCTGGCGTCCGCGTCTCTGAGCCTGTGAGTGCGTGCGCTTTCCTGCGTCCTCTTGACTGCCGGT
GCTGGGGCTCTGCGTCCTGCGTCCGCG (SEQ ID NO:1)

FIG. 2

VISUALIZING MODIFIED NUCLEOTIDES AND NUCLEIC ACID INTERACTIONS IN SINGLE CELLS

FIELD

The present disclosure relates to methods for visualizing modified nucleotides in a specific nucleic acid sequence or specific nucleic acid sequence interactions in single cells.

BACKGROUND

Epigenetics refers to heritable changes in gene expression that occur without alteration in DNA sequence. Major epigenetic processes include DNA methylation and histone covalent modification. There are numerous techniques available to study epigenetic marks at the molecular level or on a genomic scale. What is needed, however, is a technique to visualize epigenetic marks at a single genomic locus in individual cells.

SUMMARY

Among the various aspects of the present disclosure is the provision of a method for visualizing a modified nucleotide in a specific nucleic acid sequence in a cell. The method comprises a) contacting a prepared cell with at least one nucleic acid probe labeled with at least one label and having complementarity to the specific nucleic acid sequence, wherein the nucleic acid probe hybridizes with the specific nucleic acid sequence to form a hybridized cell; b) contacting the hybridized cell with a first binding agent that binds to the label of the nucleic acid probe and a second binding agent that binds to the modified nucleotide; and c) detecting the first and second binding agents by a proximity ligation assay to visualize the modified nucleotide in the specific nucleic acid sequence in the cell. In some embodiments, the prepared cell is fixed, permeabilized, and, optionally, comprises denatured chromosomal DNA. In other embodiments, the modified nucleotide is chosen from 5-methylcytidine, 3-methylcytidine, 5-hydroxymethylcytidine, 5-formylcytidine, 5-carboxylcytidine, 1-methyladenosine, 6-methyladenosine, 7-methylguanosine, xanthosine, inosine, dihydrouridine, or pseudouridine, or a modified ribose having a 2'-O-methylation. In further embodiments, the specific nucleic acid sequence is chosen from promoter DNA, enhancer DNA, CpG islands, coding DNA, intronic DNA, messenger RNA, micro RNA, noncoding RNA, long noncoding RNA, ribosomal RNA, transfer RNA, small nuclear RNA, small nucleolar RNA, SmY RNA, Y RNA, spliced leader RNA, telomerase RNA component, small interfering RNA, Piwi-interacting RNA, or trans-acting RNA. In other embodiments, the label is a haptan or dye chosen from biotin, digoxigenin, dinitrophenyl, fluorescein, diethylaminocoumarin, rhodamine, cyanine 3, cyanine 5, or texas red. In still other embodiments, the nucleic acid probe is linear or circular, comprises DNA, RNA, LNA, or a combination thereof, and has a length from about 15 nucleotides to about 500 nucleotides. In alternate embodiments, the cell is an individual cell chosen from a eukaryotic cell, a mammalian cell, a human cell, a normal cell, or a cancer cell, or the cell is within a tissue sample or fluid sample obtained from a eukaryotic organism. In some embodiments, wherein the modified nucleotide is 5-methylcytidine, and the specific nucleic acid sequence is a Septin 9 promoter.

Another aspect of the present disclosure encompasses a method for visualizing an interaction between two nucleic acid sequences in a cell. The method comprises a) contacting a prepared cell with a first nucleic acid probe comprising a first label and having complementarity to a first nucleic acid sequence and a second nucleic acid probe comprising a second label and having complementarity to a second nucleic acid sequence, wherein the first and second labels are different and the first and second nucleic acid probes hybridize with the first and second nucleic acid sequences, respectively; b) contacting the cell with a first binding agent that binds to the first label and a second binding agent that binds to the second label; and c) detecting the first and second binding agents by a proximity ligation assay to visualize the interaction between the two nucleic acid sequences in the cell. In some embodiments, the prepared cell is fixed, permeabilized, and, optionally, comprises denatured chromosomal DNA. In other embodiments, the modified nucleotide is chosen from 5-methylcytidine, 3-methylcytidine, 5-hydroxymethylcytidine, 5-formylcytidine, 5-carboxylcytidine, 1-methyladenosine, 6-methyladenosine, 7-methylguanosine, xanthosine, inosine, dihydrouridine, or pseudouridine, or a modified ribose having a 2'-O-methylation. In further embodiments, the specific nucleic acid sequence is chosen from promoter DNA, enhancer DNA, CpG islands, coding DNA, intronic DNA, messenger RNA, micro RNA, noncoding RNA, long noncoding RNA, ribosomal RNA, transfer RNA, small nuclear RNA, small nucleolar RNA, SmY RNA, Y RNA, spliced leader RNA, telomerase RNA component, small interfering RNA, Piwi-interacting RNA, or trans-acting RNA. In other embodiments, the label is a haptan or dye chosen from biotin, digoxigenin, dinitrophenyl, fluorescein, diethylaminocoumarin, rhodamine, cyanine 3, cyanine 5, or texas red. In still other embodiments, the nucleic acid probe is linear or circular, comprises DNA, RNA, LNA, or a combination thereof, and has a length from about 15 nucleotides to about 500 nucleotides. In alternate embodiments, the cell is an individual cell chosen from a eukaryotic cell, a mammalian cell, a human cell, a normal cell, or a cancer cell, or the cell is within a tissue sample or fluid sample obtained from a eukaryotic organism.

Other aspects and features of the disclosure are detailed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 presents the sequence of the SEPTIN 9 promoter and the location of the 18 oligo probes (underlined) designed to target the promoter region around the CpG island (shown in italics) of the SEPTIN 9 promoter.

FIG. 3A shows control prostate cancer (DU145) cells incubated with LacZ probes (no PLA signal) stained with DAPI. FIG. 3B and FIG. 3C show cells incubated with the SEPTIN 9 oligo probes. The PLA signal is shown in red. Two red dots per nucleus represent the diploid number of chromosome 17 in DU145 cells where SEPTIN 9 is located. FIG. 3B presents an overlay of the PLA signal and DAPI staining. FIG. 3C presents an overlay of the PLA signal and differential interference contrast (DIC).

FIG. 4A shows a PLA signal and DAPI overlay. FIG. 4B presents a DIC and PLA signal overlay.

DETAILED DESCRIPTION

Figure 1:
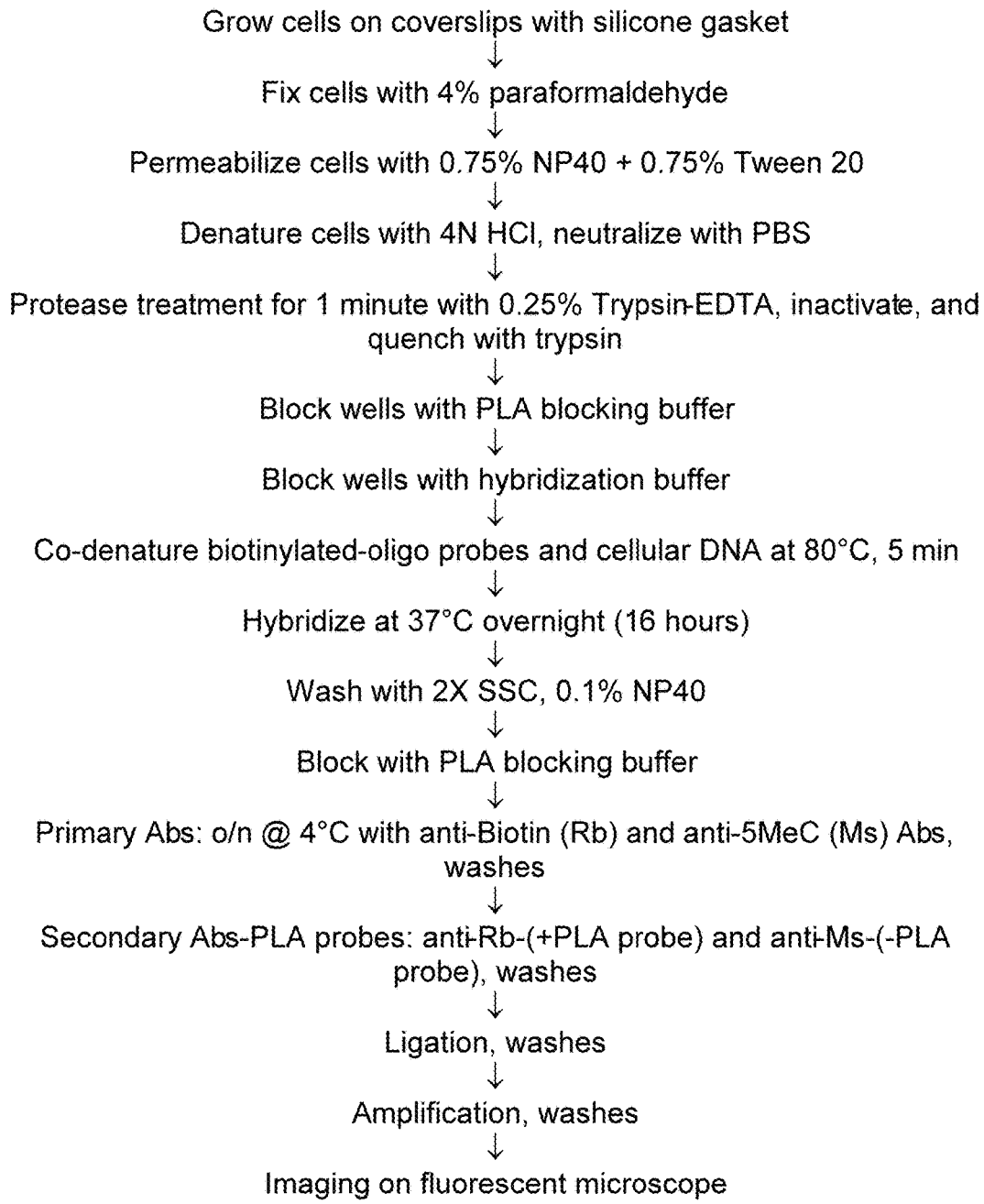
FIG. 1 outlines the in situ hybridization—proximity ligation assay (ISH-PLA) protocol.

The present disclosure provides methods for visualizing modified nucleotides in specific nucleic acids sequences or interactions between specific nucleic acid sequences and proteins or other specific nucleic acid sequences in single cells. The methods comprise coupling an in situ hybridization (ISH) reaction with a proximity ligation assay (PLA) reaction, and can be used to visualize epigenetic marks such as DNA methylation at a single genomic locus in individual cells. Many diseases, such as cancer, are associated with abnormal promoter hypermethylation. Thus, the methods disclosed herein can be used to detect cancer cells in a background of normal cells and/or used as diagnostic tools to screen cancer biopsy tissue samples.

I. Method for Visualizing Modified Nucleotides in a Cell

One aspect of the disclosure provides a method for visualizing a modified nucleotide in a nucleic acid sequence of interest in a cell. The method comprises contacting a prepared cell with at least one nucleic acid probe labeled with at least one label and having complementarity to the specific nucleic acid sequence of interest, wherein the nucleic acid probe hybridizes with the specific nucleic acid sequence. The method further comprises contacting the cell with a first binding agent that binds to the label of the nucleic acid probe and a second binding agent that binds to the modified nucleotide of interest. Lastly, the method comprises detecting the first and second binding agents by a proximity ligation assay to visualize the modified nucleotide in the specific nucleic acid sequence of interest in the cell.

(a) Step A—Hybridizing the Labeled Probe to the Specific Nucleic Acid

The first step of the method comprises an in situ hybridization reaction. This step comprises contacting a prepared cell with at least one nucleic acid probe labeled with at least one label and having complementarity to the specific nucleic acid sequence, such that the nucleic acid probe hybridizes with the specific nucleic acid sequence comprising the modified nucleotide.

(i) Modified Nucleotide

The method disclosed herein can be used to detect and visualize a variety of modified nucleotides. The modified nucleotide can be within DNA or RNA, and the nucleotide can be modified by methylation, hydroxylation, acetylation, formylation, acylation, carboxylation, thiolation, alkylation, amination, esterification, phosphorylation, or combinations thereof. Specific examples of modified nucleotides include 5-methylcytidine, 5-hydroxymethylcytidine, 5-formylcytidine, 5-carboxylcytidine, 3-methylcytidine,$N^4$-methylcytidine, $N^4$-acetycytidine, 2-thiocytidine, 1-methyladenosine, 2-methyladenosine, $N^6$-methyladenosine, $N^6,N^6$-dimethyladenosine, $N^6,N^6,N^6$-trimethyladenosine, $N^6$-isopenyladenosine, 2-methylthio-$N^6$-isopenyladenosine, 1-methylguanosine, $N^2$-methylguanosine, $N^2,N^2$-dimethylguanosine, $N^2,N^2,N^2$-trimethylguanosine, 7-methylguanosine, xanthosine, inosine, 1-methylinosine, dihydrouridine, pseudouridine, 1-methylpseudouridine, 3-methyluridine, 5-methyluridine, 5-methylaminomethyluridine, 5-methoxyaminomethyl-2-thiouridine, 5-carboxymethyluridine, 5-methoxycarbonylmethyl-2-thiouridine, 5-methoxycarbonylmethyluridine, 5-methoxyuridine, 5-carboxymethyaminomethyluridine, 5-carboxymethyaminomethyl-2-thiouridine, uridine-5-oxyacetic acid methyl ester, uridine-5-oxyacetic acid, 5-methyl-2-thiouridine, 2-thiouridine, 4-thiouridine, wybutoxosine, wybutosine, queuosine, ribosylthymine, pyrimidine dimers, and 2'-O-methyl derivatives of standard or modified ribonucleotides. In specific embodiments, the modified nucleotide is 5-methylcytidine.

(ii) Specific Nucleic Acid Sequence

The specific nucleic acid sequence comprising the modified nucleotide can and will vary. Non-limiting examples of suitable nucleic acid sequences include chromosomal DNA, transcriptional control regions of DNA, promoter DNA, CpG, enhancer DNA, silencer DNA, locus control regions of DNA, protein-coding DNA, intronic DNA, RNA-coding DNA, episomal DNA, viral RNA, messenger RNA (mRNA), micro RNA (miRNA), noncoding RNA (ncRNA), long noncoding RNA (lncRNA), ribosomal RNA (rRNA), transfer RNA (tRNA), small nuclear RNA (snRNA), small nucleolar RNA (snoRNA), SmY RNA, Y RNA, spliced leader RNA (SL RNA), telomerase RNA component (TERC), small interfering RNA (siRNA), Piwi-interacting RNA (piRNA), or trans-acting RNA (rasiRNA).

The identity of the specific nucleic acid sequence comprising the modified nucleotide can and will vary, provided that the sequence of all or part of the specific nucleic acid sequence is known. In some embodiments, the specific nucleic acid sequence can be a region of a chromosomal sequence (i.e., gene) encoding a protein associated with a disease or disorder associated with aberrant gene expression. Aberrant gene expression can be associated with hypermethylated or hypomethylated promoter control regions. Non-limiting examples of diseases or disorders associated with aberrant gene expression include cancer (e.g., colon, stomach, pancreatic, liver, kidney, bladder, rectal, lung, breast, ovarian, cervical, brain, glioma, leukemia, melanoma, prostate, and head and neck cancers), autoimmune diseases (such as Type 1 Diabetes, inflammatory bowel disease), inflammatory diseases (such as asthma), and metabolic disorders. For example, non-limiting examples of genes associated with cancer include Septin 9, ATM, APC, BRCA1, BRCA2, CDH1, E-Cad, CDKN2B, DAPK, FANCB, FANCF, GATA-4, GATA-5, GSTP1, HER2, HIC1, MGMT, MLH1, MSH2, MSH4, NEIL1, PITX2, p14ARF, p15INK4B, p16INK4A, p53, p73, RAD51C, RASSF1, RB, TIMP3, VHL, and WRN. Examples of genes associated with autoimmune or inflammatory diseases or disorders include, but are not limited to, AAA1, ABCB1, ARTS-1, ATG16L1, BSN, CLSTN3, CTLA4, ERBB3, FCER1A, GSTP1, GSDML, HLA, HLA-DQA1, IFIH1, IL2Ra, IL23R, IBD5, IRGM, JAZF1, KIQQ1109, LNPEP, LPP, MYO9B, MST, NKKX2-3, NELL1, NOD2, NOTCH2, PLA2G7, PPATG, PTPN2, RGS1, SH2B3, TAGAP, THADA, TNF, and WSF1. In other embodiments, the modified nucleotide can be in a specific mRNA sequence (e.g., a transcript of any of the genes listed above), a specific miRNA (e.g., miRNAs associated with colon cancer include miR-551a, miR-552, miR-138, miR-451, miR-144, miR548h, miR-658, miR-595, miR-338-3p, etc.), or a specific lncRNA (e.g., RepA, HOTAIR, Airnm, Kcnq1ot1, Evf-2, HSR1, SRA, NRON, MALAT1, NEAT2, etc.).

(iii) Nucleic Acid Probe

The nucleic acid probe (or probes) used in the method is labeled with at least one label and has complementarity to the specific nucleic acid sequence comprising the modified nucleotide. The nucleic acid probe can be DNA, RNA, LNA, PNA, or combinations thereof; can comprise standard nucleotides or nucleotide analogs; and can comprise standard sugar-phosphate backbone or a modified backbone (e.g., phosphorothioate). The nucleic acid probe can be single stranded, or the nucleic acid probe can be double-stranded (and denatured prior to use). The nucleic acid probe can be linear or circular, and can comprise secondary structures (e.g., hairpins, loops, stems, bulges, etc.).

The length of the nucleic acid probe can vary. For example, the nucleic acid probe can range in length from about 10 nucleotides to several thousand nucleotides in length. In some embodiments, the nucleic acid probe can be from about 10 to 30 nucleotides in length, from about 15 to 25 nucleotides in length, or about 20 nucleotides in length. In other embodiments, the nucleic acid probe can be from about 15 to 500 nucleotides, from about 30 to 100 nucleotides, from about 100 to 300 nucleotides, from about 300 to about 1000 nucleotides, or from about 1000 to about 10,000 nucleotides in length. In various embodiments, therefore, the nucleic acid probe can be about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, or 10,000 nucleotides in length, or any integer falling between a given adjacent set of the foregoing integers (e.g., 11, 12, 13, or 14, 16, 17, 18, or 19; 21, 22, 23, or 24, and so on).

The nucleic acid probe is labeled with at least one label. The label can be a haptan or a dye. Non-limiting examples of suitable haptans and dyes include biotin, digoxigenin, dinitrophenyl, fluorescein, diethylaminocoumarin, rhodamine, cyanine 3, cyanine 5, and texas red. In some embodiments, the label can be located at the 5'-end or the 3'-end of the nucleic acid probe. For example, the label can be attached to either end of the nucleic acid probe via a linker (e.g., tetra-ethylene glycol (TEG) spacers, polyethylene glycol (PEG) spacers, C6 linker, or another linker known in the art). In other embodiments, the label can be located throughout the nucleic acid probe, i.e., the nucleic acid probe can comprise labeled nucleotides.

The nucleic acid probe can be chemically or enzymatically synthesized. In one embodiment, the nucleic acid probe can be synthesized using standard phosphoramidite solid-phase synthesis techniques. The resultant probe can be end-labeled with the label using standard procedures. In another embodiment, a labeled DNA probe can be synthesized by nick translation in the presence of labeled nucleotides (e.g., labeled dATP or labeled dCTP). In still another embodiment, a labeled RNA probe can be synthesized by in vitro transcription in the presence of using labeled ribonucleotides (e.g., labeled UTP).

The nucleic acid probe is designed to have complementarity to the specific nucleic acid of interest (i.e., can base pair with the specific nucleic acid of interest). In various embodiments, the nucleic acid probe can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence complementarity to the specific nucleic acid of interest. In specific embodiments, the nucleic acid probe has at least about 90% or 95% sequence complementarity to the specific nucleic acid of interest.

In some embodiments, the nucleic acid probe comprises a population of short nucleic acid sequences with each having complementarity to an adjacent region of the specific nucleic acid of interest with general, such that upon hybridization, the nucleic acid probes "tile" the specific nucleic acid of interest. In other embodiments, the nucleic acid probe is a longer nucleic acid sequence comprising labeled nucleotides throughout the length of the probe.

(iv) Cells

A variety of cells can be used in the method disclosed herein. In general, the cell is a eukaryotic cell. In various aspects, the cell can be a human cell, a non-human mammalian cell, a non-mammalian vertebrate cell, an invertebrate cell, an insect cell, a plant cell, a yeast cell, or a single cell eukaryotic organism. The cell can be a normal cell, an abnormal cell, or a cancerous cell. The cell can be a primary cell or a cell line cell. The cell may be an adult cell or an embryonic cell (e.g., an embryo). In still other aspects, the cell can be a stem cell. Suitable stem cells include without limit embryonic stem cells, ES-like stem cells, fetal stem cells, adult stem cells, pluripotent stem cells, induced pluripotent stem cells, multipotent stem cells, oligopotent stem cells, unipotent stem cells and others. In exemplary aspects, the cell is a mammalian cell.

In some embodiments, the cell can be a human cell line cell. Non-limiting examples of suitable cell lines include DU145 (metastatic cancer), SW490 (colon cancer), DLD-1 (colon cancer), KM20L2 (colon cancer), COLO 205 (colon cancer), HCC-2998, (colon cancer), HCT-116 (colon cancer), HCT-15 (colon cancer), HT29 (colon cancer), KM12 (colon cancer), SW-620 (colon cancer), SF-268 (CNS), SF-295 (CNS), SF-539 (CNS), SNB-19 (CNS), SNB-75 (CNS), U251 (CNS), CCRF-CEM (leukemia), HL-60(TB) (leukemia), K-562 (leukemia), MOLT-4 (leukemia), RPMI-8226 (leukemia), SR (leukemia), A549 (non-small cell lung cancer), EKVX (non-small cell lung cancer), HOP-62 (non-small cell lung cancer), HOP-92 (non-small cell lung cancer), NCI-H226 (non-small cell lung cancer), NCI-H23 (non-small cell lung cancer), NCI-H322M (non-small cell lung cancer), NCI-H460 (non-small cell lung cancer), NCI-H522 (non-small cell lung cancer), LOX IMVI (melanoma), MALME-3M (melanoma), M14 (melanoma), MDA-MB-435 (melanoma), SK-MEL-2 (melanoma), SK-MEL-28 (melanoma), SK-MEL-5 U(melanoma), ACC-257(melanoma), UACC-62 (melanoma), IGR-OV1 (ovarian), OVCAR-3 (ovarian), OVCAR-4 OVCAR-5 (ovarian), OVCAR-8 (ovarian), SK-OV-3 (ovarian), 786-0 (renal), A498 (renal), ACHN (renal), CAKI-1 (renal), RXF 393 (renal), SN12C (renal), TK-10 (renal), UO-31 (renal), PC-3 (prostate), DU-145 (prostate), MCF7 (breast), MDA-MB-231 (breast), MDA-MB-468 (breast), HS 578T (breast), BT-549 (breast), and T-47D (breast).

In other embodiments, the cell can be a mammalian cell line cell, Non-limiting examples of suitable mammalian cell lines include Chinese hamster ovary (CHO) cells, baby hamster kidney (BHK) cells; mouse myeloma NSO cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells;

mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76) cells; and human embryonic kidney cells (HEK293, HEK293T). An extensive list of mammalian cell lines may be found in the American Type Culture Collection catalog (ATCC, Manassas, Va.).

In still other embodiments, the cell can be within a tissue sample or fluid sample obtained from a subject. For example, a tissue sample or fluid sample can be removed by surgical resection, excisional biopsy, incisional biopsy, core biopsy, or needle aspiration biopsy. The subject can be a human, non-human mammal (e.g., rodent, cat, dog, livestock animal, and the like), or a non-mammalian vertebrate (e.g., fish, birds, and so forth). The tissue sample can be frozen or fixed using a fixative as detailed below. The fixed tissue sample can be embedded in an embedding medium such as paraffin, paraplast, or similar embedding medium.

(v) Preparing the Cell

The cell is prepared for in situ hybridization by fixing the cell, permeabilizing the cell, and, optionally, denaturing the chromosomal DNA of the cell. A variety of fixatives can be used to fix or crosslink the cell. Examples of suitable fixatives include acetone, acetic acid, ethanol, formaldehyde (or formalin, a 37% aqueous solution of formaldehyde), glutaraldehyde, iodoform, lactic acid, methanol, paraformaldehyde, picric acid, and combinations thereof. In specific embodiments, the fixative can be paraformaldehyde. The concentration of fixative and during of the fixation process will vary depending upon the type of cell (e.g., cell line cell or cell in a tissue).

The fixed cell is permeabilized by incubation with a solution comprising at least one surfactant and/or protease. Non-limiting examples of suitable surfactants include Tween-20, Tween-80, Triton X-100, cetyl alcohol, decyl glucoside, digitonin, lauryl glucoside, IGEPAL CA-630, leucoperm, NP-40, nonoxynol-9, octaethylene glycol monododecyl ether, n-octyl β-D-thioglucopyrenoside, oleyl alcohol, octyl glucoside, Polysorbate 20, Polysorbate 80, saponin, stearyl alcohol, or combinations thereof. Suitable proteases include, without limit, Proteinase K, caspase, chymotrypsin, papain, pepsin, and trypsin. In some embodiments, the cell is incubated with a solution comprising Tween-20 and/or Triton X-100. The concentration of the surfactant or protease and the duration of the incubation period can and will vary depending upon the type of cell, tissue, or fluid.

In embodiments in which the specific nucleic acid sequence comprising the modified nucleotide is double stranded, the cell is contacted with a denaturing solution to convert double-stranded nucleic acids into single-stranded nucleic acids. The denaturing solution can be acidic or it can be alkaline. An acidic solution comprises an acid such as hydrochloric acid, and an alkaline solution comprises a base such as an alkali metal hydroxide (e.g., sodium or potassium hydroxide). The concentration of the acid or base in the denaturing solution and the duration of the denaturation step can and will vary depending upon depending upon the type of cell, tissue, or fluid.

Following nucleic acid denaturation, the cell can be contacted with a protease(s) to remove proteins from the nucleic acid, thereby making the specific nucleic acid more accessible to the nucleic acid probe. Non-limiting examples of suitable proteases include caspase, chymotrypsin, papain, pepsin, Proteinase K, trypsin, and combinations thereof. The concentration of the protease and the duration of the incubation period can and will vary depending upon the type of cell, tissue, or fluid.

In some embodiments, the cell may be within a tissue sample or a section of a tissue sample. The sample may be a frozen sample or a formalin-fixed paraffin-embedded (FFPE) sample. In situations in which the sample is a frozen sample, the cells may be fixed and permeabilized, the chromosomal DNA may be denatured, and the cells may be contacted with proteases essentially as described above. In situations in which the sample is a FFPE sample, the sample may be de-paraffinized using xylenes or other organic solvents, the cells may be permeabilized, the chromosomal DNA may be denatured, and the cells may be contacted with proteases essentially as described above.

(vi) Hybridization

The method comprises contacting the prepared cell with the labeled nucleic acid probe to form a hybridized cell in which the labeled nucleic acid probe is base paired with the specific nucleic acid sequence comprising the modified nucleotide. For this, the prepared cell is incubated with the labeled nucleic acid probe under conditions that allow hybridization within the cell (in situ) between the labeled nucleic acid probe and the nucleic acid sequence of interest. In situ hybridization protocols and in situ hybridization solutions are known in the art. In specific embodiments, the hybridization solution can contain 50% formamide, 10% Ficoll 400, 0.1% SDS, and 2×SSC (saline-sodium citrate). The temperature and duration of the hybridization reaction can vary depending upon the type of cell or tissue. For example, in embodiments in which the cell is a cultured cell, the hybridization can be performed at about 37° C. for about 16 hours.

(b) Step B—Binding of the First and Second Binding Agents

The method further comprises contacting the hybridized cell comprising the hybridized nucleic acid probe-specific nucleic acid sequence complex with a first binding agent that binds to the label of the nucleic acid probe and a second binding agent that binds to the modified nucleotide of interest. Each of the first and second binding agents independently can be a protein, an antibody (e.g., a monoclonal antibody or polyclonal antibody), an antibody fragment (e.g., a Fc fragment or a Fab fragment), a nucleic acid, or an aptamer. In specific embodiments, each of the first and second binding agents is an antibody, wherein each antibody is prepared in a different species. For example, the first binding agent can be a rabbit polyclonal antibody that recognizes the label in the labeled nucleic acid probe, and the second binding agent can be mouse monoclonal that recognizes the modified nucleotide. Methods for incubating cells with antibodies are well known to those of skill in the art, as are suitable solutions (e.g. blocking solutions, rinse or wash solutions, incubation solutions, etc.).

(c) Step C—Detecting the First and Second Binding Agents

The method further comprises detecting the first and second binding agents that are in close proximity. The first binding agent binds to the label of the hybridized nucleic acid probe, and the second binding agent binds to each and every modified nucleotide within the cell. In order to detect the first and second binding agents that are bound to the hybridized nucleic acid probe-specific nucleic acid sequence complex (and thus, detect the modified nucleotide in the specific nucleic acid sequence of interest), a proximity ligation assay (PLA) is used to detect first and second binding agents that are in close proximity (i.e., within about 40 nm, Gomez et al., 2013, Nature Methods, 10 (2):171-177). PLA kits are commercially available (e.g., DUOLINK®, Sigma-Aldrich). The PLA signal can be detected and analyzed using standard fluorescence microscopy and image analysis software programs.

(d) Specific Embodiment

In one embodiment, the modified nucleotide can be 5-methylcytidine, the specific nucleic acid sequence can be Septin 9 promoter DNA, and the cells can be human cancer cells (e.g., colon cancer cells). The specific nucleic acid sequence can be labeled with biotin and the first binding agent can be anti-biotin polyclonal antibody raised in rabbit. The second binding agent can be anti-5-methylcytosine monoclonal antibody raised in mouse.

II. Method for Visualizing Nucleic Acid Interactions in a Cell

A further aspect of the present disclosure provides a method for visualizing interactions between specific nucleic acids in a cell. The method comprises contacting a prepared cell with a first nucleic acid probe comprising a first label and having complementarity to a first nucleic acid sequence and a second nucleic acid probe comprising a second label and having complementarity to a second nucleic acid sequence, wherein the first and second labels are different and the first and second nucleic acid probes hybridize with the first and second nucleic acid sequences, respectively. The method further comprises contacting the cell with a first binding agent that binds to the first label and a second binding agent that binds to the second label, and then detecting the first and second binding agents by a proximity ligation assay to visualize the interaction between the two nucleic acids in the cell.

A variety of nucleic acid interactions can be detected using the disclosed method. Non-limiting examples include interactions between RNA and DNA (e.g., noncoding RNAs or functional RNAs interacting with specific chromosomal sequences during transcription, replication, recombination, repair, or another nuclear process), interactions between different classes of RNA (e.g., during RNA processing, slicing, translation, nuclear translocation, and other cellular events). Examples of suitable nucleic acids are detailed above in section I(a)(ii).

Each of the first and second nucleic acid probes are essentially as described above in section I(a)(iii), however each of the first and second nucleic acid probes is labeled with a different label. In one embodiment, the first nucleic acid probe can be labeled with biotin and the second nuclei acid probe can be labeled with digoxigenin. In another embodiment, the first nucleic acid probe can be labeled with biotin and the second nucleic acid probe can be labeled with fluorescein (e.g., fluorescein isothiocyanate, FITC).

As various changes could be made in the above-described methods without departing from the scope of the invention, it is intended that all matter contained in the above description and in the examples given below, shall be interpreted as illustrative and not in a limiting sense.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some of the base pairs are complementary. The bases that are not complementary are "mismatched." Complementarity may also be complete (i.e., 100%), if all the base pairs of the duplex region are complementary.

The term "CpG island" refers to a cluster of CpG sites, wherein a CpG site refers to regions of DNA where a cytosine nucleotide occurs next to a guanine nucleotide in the linear sequence of bases along its length, where "CpG" is an abbreviation for a "-C-phosphate-G-" linkage, i.e. cytosine and guanine separated by a single phosphate.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O- methyl nucleotides, locked nucleic acids (LNA), peptide nucleic acids (PNA), and morpholinos.

The terms "polypeptide" and "protein" are used interchangeably to refer to a polymer of amino acid residues.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website.

EXAMPLES

The following example illustrates certain aspects of the invention.

Example 1

Visualizing DNA Methylation on SEPTIN 9 Promoter in Individual Cancer Cells

The purpose of the following example was to develop a highly sensitive detection method to detect DNA methylation at a single genomic locus in individual cells. With this aim, a protocol was developed to perform in-situ hybridization followed by proximity ligation assay (PLA) (a.k.a., DUOLINK®, Sigma-Aldrich) and cell imaging to visualize DNA-methylation (5 meC) on the SEPTIN 9 promoter. SEPTIN 9 promoter methylation is a known biomarker for colon cancer (Wasserkort et al, 2013, BMC Cancer, 13:398), After optimizing cell cross-linking (i.e., fixing), cell permeabilization, and chromatin accessibility, the genomic specificity was ascertained by hybridizing with a pool of biotinylated-oligo probes that targeted the CpG island in the human SEPTIN 9 promoter. The PLA assay was performed using anti-biotin and anti-5 meC antibodies, corresponding (+ and −) PLA probes, and Far Red detection reagents. FIG. 1 outlines the strategy.

Oligo (20-mer) probes were designed against the human SEPTIN 9 sequence using free online software (i.e., Stellaris FISH Probe Designer). Probes were synthesized by Sigma Custom Products with the 3'TEG-Biotin modification and purified by HPLC. FIG. 2 presents the SEPTIN 9 promoter sequence and shows the location of the 18 oligo probes.

Human cancer cells, i.e., DU145 (metastatic cancer; origin in prostrate migrated to brain) or SW480 (colon cancer), were grown in DMEM (Dulbecco's Modified Eagle's Medium) supplemented with 10% FBS and Pen/Strep antibiotics, and seeded (~$10^4$ cells) per well of 8-well culture chambered coverglass plates (with silicone gasket). The cells were washed twice with HBSS, and then fixed with 4% paraformaldehyde solution (40 μL/well, 16% paraformaldehyde stock diluted 1:4 in 1×PBS) for 30 minutes at room temperature (RT). The crosslinking was stopped by adding 5 μL/well of 1.25M Glycine, and incubating at RT for 5 minutes. The cells were permeabilized by incubation for 1 hour at RT with permeabilization buffer (0.75% Tween 20 and 0.75% Triton X-100 in 1×PBS). The cells were rinsed with 1×PBS. For detection of 5-meC DNA, the cells were treated with 4 N HCL for 10 minutes at RT. The cells were washed with 1×PBS for 30 min at RT. The cells were treated for 1 minute with pre-warmed (37° C.) 0.25% Trypsin-EDTA solution, and the trypsin was inactivated by incubating for 2 minutes in pre-warmed (37° C.) quenching solution (i.e., DMEM supplemented with 10% FBS and 3 mg/mL BSA). The cells were washed with 1×PBS and blocked with an in situ hybridization blocking solution for 1 hour at RT.

The cells were incubated with hybridization buffer (50% Formamide, 10% Ficoll 400, 0.1% SDS, 2×SSC) made in water for 30 minutes at 37° C. using a slide hybridizer (Abbott Molecular). The oligo probes were denatured by addition of hybridization buffer, and the probes (i.e., (i) all 18 SEPTIN 9 probes, (ii) the 5 SEPTIN 9 probes closest to the CpG island, or (iii) LacZ control probes; 100 μM each) were added to the wells, which were sealed with hybridization covers, and the slide hybridizer denaturation/hybridization program was run (i.e., denature at 80° C. for 5 minutes followed by hybridization at 37° C. for 16 hours). The cells were washed three time with wash buffer (2×SSC, 0.1% NP-40), and then subjected to the PLA protocol starting with the blocking step. Antibodies used were anti-biotin (Abcam 53494, polyclonal antibody raised in rabbit, 1:200 dilutions in PLA antibody diluent) and the anti-5-methy-cytosine (Eurogentec BI-MECY-0100, monoclonal antibody raised in mouse, 1:200 dilution in PLA antibody diluent).

Figure 3A:
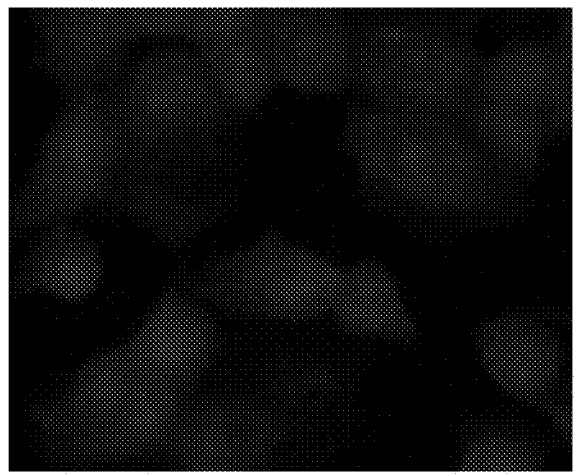
FIG. 3A, FIG. 3B, and FIG. 3C illustrate the visualization of SEPTIN 9 promoter methylation in prostate cancer cells (DU145).
Figure 3B:
Figure 3C:
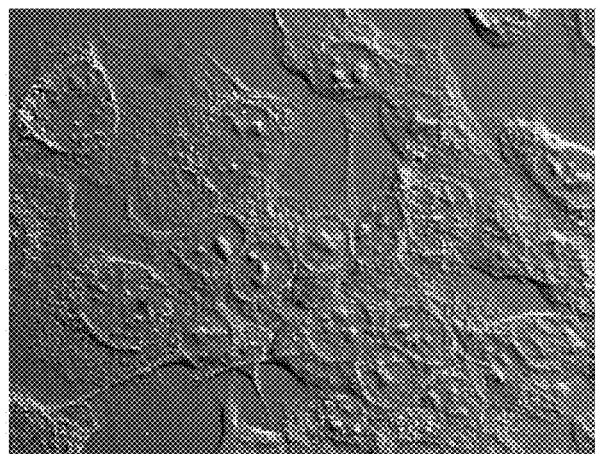

The SEPTIN 9 gene is located on human chromosome 17. Thus, in a cancer cell line that is diploid for chromosome 17 and has both copies of the SEPTIN 9 promoter methylated; one would expect to see two punctate PLA (red) dots in the nuclei of the cells. This was observed in several DU145 cells (FIGS. 3B and 3C) that were incubated with Septin 9 promoter-specific probes (i.e., probe set (ii) oligos #5-9, surrounding the methylated CpG island). Similar data were obtained with probe set (i) (data not shown) but not with the non-specific LacZ probes (FIG. 3A). No PLA signal was observed in normal foreskin fibroblasts cells (BJ) or pancreatic cancer cells (BxPC3), data not shown.

Figure 4A:
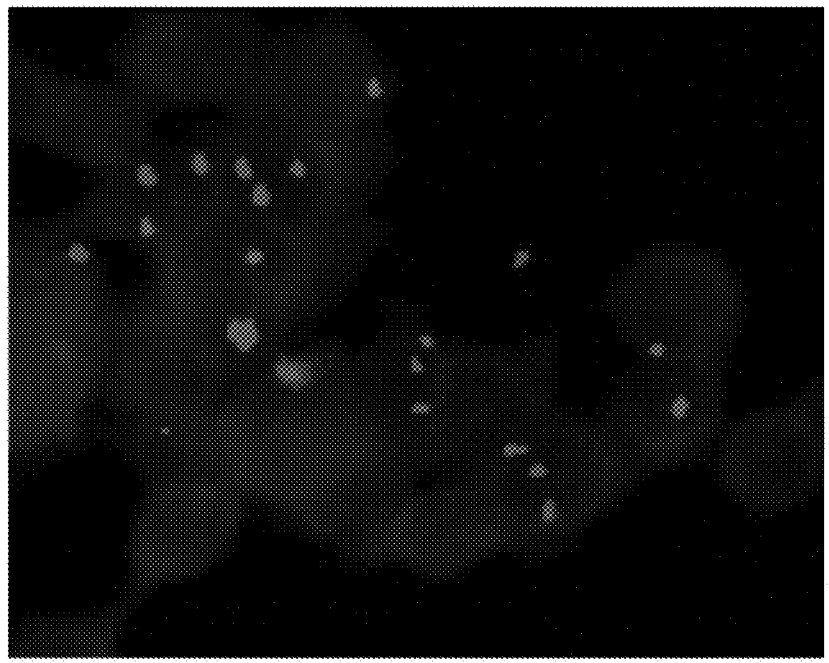
FIG. 4A and FIG. 4B show SEPTIN 9 promoter methylation in colon cancer cells (SW480). The PLA signal is shown in red. Three red dots per nucleus represent the triploid number of chromosome 17 in SW480 cell where SEPTIN 9 is located.
Figure 4B:
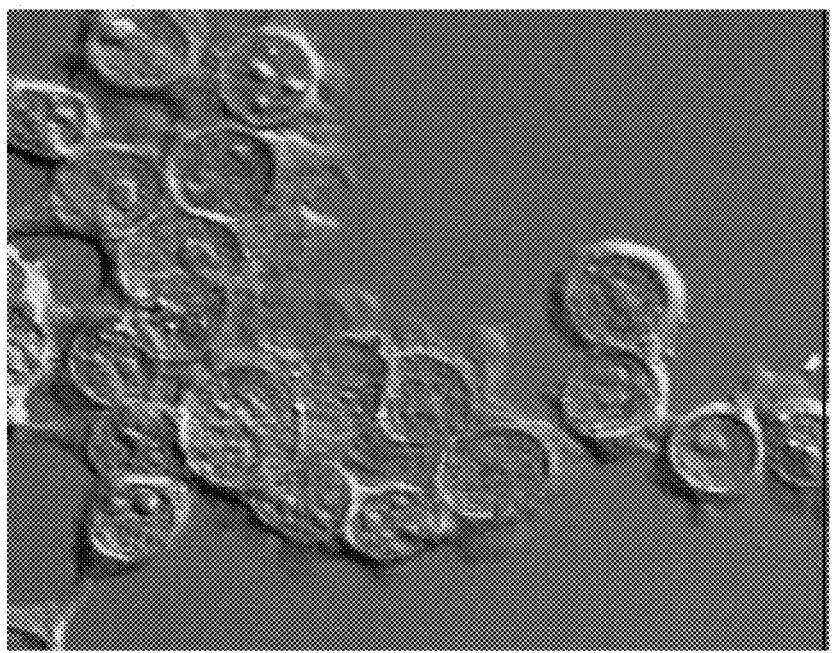
Figure 5:
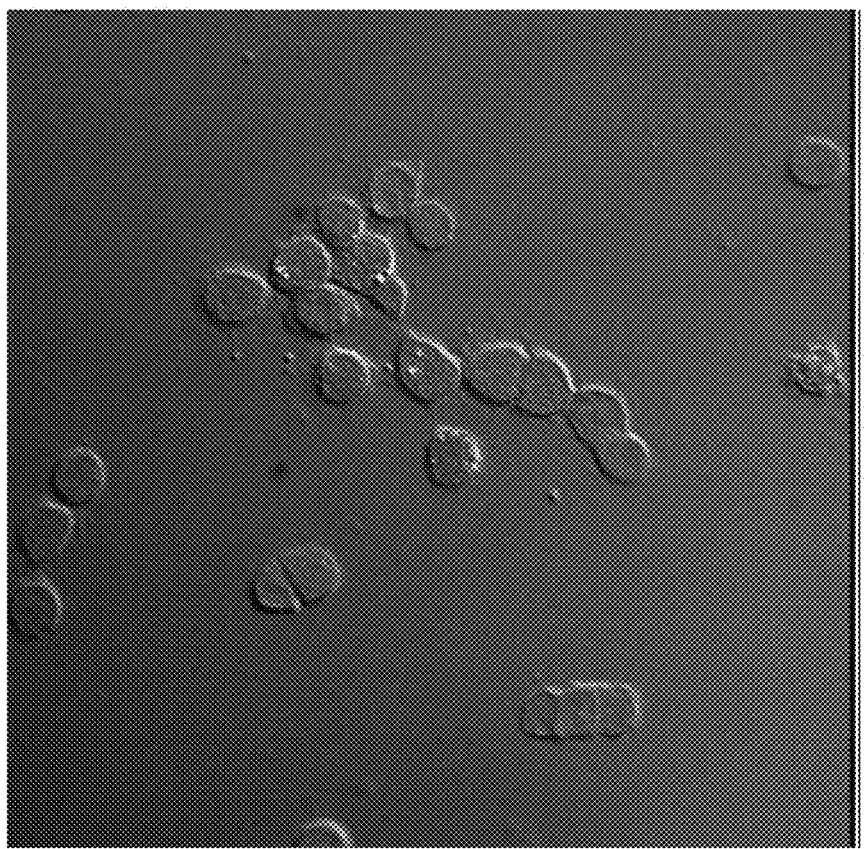
FIG. 5 illustrates that SEPTIN 9 promoter methylation is diminished following 5-AzaC treatment of SW480 cells. A few drug treated cells showed cytotoxic effects in terms of altered cellular shape that resulted in trapping the PLA-probe and accounted for the diffuse non-specific red fluorescence observed in a few cells.

Specificity of methylated SEPTIN 9 promoter detection was further confirmed by performing the same ISH-PLA assay in colon cancer cell line SW480, which is triploid for chromosome 17. Indeed, three PLA dots per nuclei were observed in several SW480 cells when hybridized with SEPTIN 9 probe set (ii) (FIGS. 4A and 4B) but not with LacZ probes (data not shown). Loss of this nuclear ISH-PLA signal in SW480 cells that were treated with 5-Azacytidine (5-AzaC, 500 nM for 24 hours), a drug known to block DNA methylation in vivo, confirmed the 5-meC epitope dependent nature of the PLA signal (FIG. 5). A few drug treated cells showed cytotoxic effects in terms of altered cellular shape that resulted in trapping the PLA-probe and accounted for the diffuse non-specific red fluorescence observed in a few cells. 5-AzaC is a pyrimidine nucleoside analogue of cytidine with antineoplastic activity. Azacitidine is incorporated into DNA, where it reversibly inhibits DNA methyltransferase, thereby blocking DNA methylation.

What is claimed is:

1. A method for visualizing a modified nucleotide in a specific nucleic acid sequence in a cell, the method comprising:
   a) contacting a prepared cell with at least one nucleic acid probe labeled with at least one label and having complementarity to the specific nucleic acid sequence, wherein the nucleic acid probe hybridizes with the specific nucleic acid sequence to form a hybridized cell;
   b) contacting the hybridized cell with a first binding agent that binds to the label of the nucleic acid probe and a second binding agent that binds to the modified nucleotide;
   c) detecting the first and second binding agents by a proximity ligation assay to visualize the modified nucleotide in the specific nucleic acid sequence in the cell.

2. The method of claim 1, wherein the prepared cell is fixed, permeabilized, and, optionally, comprises denatured chromosomal DNA.

3. The method of claim 1, wherein the modified nucleotide is chosen from 5-methylcytidine, 3-methylcytidine, 5-hydroxymethylcytidine, 5-formylcytidine, 5-carboxylcytidine, 1-methyladenosine, 6-methyladenosine, 7-methylguanosine, xanthosine, inosine, dihydrouridine, or pseudouridine, or a modified ribose having a 2'-O-methylation.

4. The method of claim 1, wherein the specific nucleic acid sequence is chosen from promoter DNA, enhancer DNA, CpG island DNA, coding DNA, intronic DNA, messenger RNA, micro RNA, noncoding RNA, long noncoding RNA, ribosomal RNA, transfer RNA, small nuclear RNA, small nucleolar RNA, SmY RNA, Y RNA, spliced leader RNA, telomerase RNA component, small interfering RNA, Piwi-interacting RNA, or trans-acting RNA.

5. The method of claim 1, wherein the label is a haptan or dye chosen from biotin, digoxigenin, dinitrophenyl, fluorescein, diethylaminocoumarin, rhodamine, cyanine 3, cyanine 5, or texas red.

6. The method of claim 1, wherein the nucleic acid probe is linear or circular, comprises DNA, RNA, LNA, or a combination thereof, and has a length from about 15 nucleotides to about 500 nucleotides.

7. The method of claim 1, wherein the cell is an individual cell chosen from a eukaryotic cell, a mammalian cell, a human cell, a normal cell, or a cancer cell, or the cell is within a tissue sample or fluid sample obtained from a eukaryotic organism.

8. The method of claim 1, wherein the modified nucleotide is 5-methylcytidine, and the specific nucleic acid sequence is a Septin 9 promoter.

9. A method for visualizing an interaction between two nucleic acid sequences in a cell, the method comprising:
   a) contacting a prepared cell with a first nucleic acid probe comprising a first label and having complementarity to a first nucleic acid sequence and a second nucleic acid probe comprising a second label and having complementarity to a second nucleic acid sequence, wherein the first and second labels are different and the first and second nucleic acid probes hybridize with the first and second nucleic acid sequences, respectively;
   b) contacting the cell from step a) with a first binding agent that binds to the first label and a second binding agent that binds to the second label;
   c) detecting the first and second binding agents by a proximity ligation assay to visualize the interaction between the two nucleic acid sequences in the cell.

10. The method of claim 9, wherein the prepared cell is fixed, permeabilized, and, optionally, comprises denatured chromosomal DNA.

11. The method of claim 9, wherein each of the first and second nucleic acid sequences is chosen from promoter DNA, enhancer DNA, CpG island DNA, coding DNA, intronic DNA, messenger RNA, micro RNA, noncoding RNA, long noncoding RNA, ribosomal RNA, transfer RNA, small nuclear RNA, small nucleolar RNA, SmY RNA, Y RNA, spliced leader RNA, telomerase RNA component, small interfering RNA, Piwi-interacting RNA, or trans-acting RNA.

12. The method of claim 9, wherein each of the first, and second labels is chosen from biotin, digoxigenin, dinitrophenyl, fluorescein, diethylaminocoumarin, rhodamine, cyanine 3, cyanine 5, or texas red.

13. The method of claim 9, wherein each of the first and second nucleic acid probes is linear or circular, comprises DNA, RNA, LNA, or a combination thereof, and has a length from about 15 nucleotides to about 500 nucleotides.

14. The method of claim 9, wherein the cell is an individual cell chosen from a eukaryotic cell, a mammalian cell, a human cell, a normal cell, or a cancer cell, or the cell is within a tissue sample or fluid sample obtained from a eukaryotic organism.

* * * * *

SEQUENCE LISTING

<160> NUMBER OF SEQ ID NOS: 1

<210> SEQ ID NO 1
<211> LENGTH: 1819
<212> TYPE: DNA
<213> ORGANISM: Homo sapiens

<400> SEQUENCE: 1

```
gcgtcgcccg tccctggctt ctctgacagc cgtgttccat ccccgccctg tgccccttct      60
cccggacagt gccttctcca gggctcaccc aggagggtgc agcggtggcc cccggggcgg     120
tggtcgtggt gggggtgtta gctgcagggg tgccctcggg gggtgggagt tggtggcctc     180
tcgctggtgc catgggactc gcatgttcgc cctgcgcccc tcggctcttg agcccacagg     240
ccgggatcct gcctgccagc cgcgtgcgct gccgtttaac ccttgcaggc gcagagcgcg     300
cggcggcggt gacagagaac tttgtttggc tgcccaaata cagcctcctg cagaaggacc     360
ctgcgcccgg ggaaggggag gaatctcttc ccctctgggc gcccgccctc ctcgccatgg     420
cccggcctcc acatccgccc acatctggcc gcagcggggc gcccgggggg aggggctgag     480
gccgcgtctc tcgccgtccc ctgggcgcgg gccaggcggg gaggagggggg gcgctccggt     540 cgtgtgccca ggactgtccc ccagcggcca ctcgggcccc agcccccag gcctggcctt     600 gacaggcggg cggagcagcc agtgcgagac agggaggccg gtgcgggtgc gggaacctga     660
tccgcccggg aggcgggggc ggggcggggg cgcagcgcgc ggggaggggc cggcgcccgc     720
cttcctcccc cattcattca gctgagccag ggggcctagg ggctcctccg gcggctagct     780
ctgcactgca ggagcgcggg cgcggcgccc cagccagcgc gcagggcccg ggccccgccg     840
ggggcgcttc ctcgccgctg ccctccgcgc gacccgctgc ccaccagcca tcatgtcgga     900
ccccgcggtc aacgcgcagc tggatgggat catttcggac ttcgaaggtg ggtgctgggc     960
tggctgctgc ggccgcggac gtgctggaga ggaccctgcg ggtgggcctg gcgcgggacg    1020
ggggtgcgct gaggggagac gggagtgcgc tgagggggaga cgggacccct aatccaggcg    1080
ccctcccgct gagagcgccg cgcgcccccg gccccgtgcc cgcgccgcct acgtggggga    1140
ccctgttagg ggcacccgcg tagaccctgc gcgccctcac aggaccctgt gctcgttctg    1200
cgcactgccg cctgggtttc cttccttta ttgttgtttg tgtttgccaa gcgacagcga    1260
cctcctcgag ggctcgcgag gctgcctcgg aactctccag gacgcacagt ttcactctgg    1320
gaaatccatc ggtcccctcc cttggctct ccccggcggc tctcgggccc cgcttggacc    1380
cggcaacggg atagggaggt cgttcctcac ctccgactga gtggacagcc gcgtcctgct    1440
cgggtggaca gccctccccct cccccacgcc agtttcgggg ccgccaagtt gtgcagcccg    1500
tgggccggga gcaccgaacg gacacagccc aggtcgtggc agggtctaga gtgggatgtc    1560
ccatggcccc catccaggcc tggggatatc ctcatccgcc tcccagaatc gggccgtggg    1620
ggacagaagg ggcctgcgtg cggcaggga gagtatttg gctctctcct gtcttcgggg    1680
tttacaaagt gtgttggac ttgcgggct gctctgtcca agcctgggtc tggcgtccgc    1740
```

```
gtctctgagc ctgtgagtgc gtgcgctttc ctgcgtcctc ttgactgccg gtgctggggc    1800
tctgcgtcct gcgtccgcg                                                 1819
```